United States Patent
Zimin, Sr.

[11] Patent Number: 6,080,213
[45] Date of Patent: Jun. 27, 2000

[54] STABILIZED AQUEOUS DIAZO SOLUTIONS

[75] Inventor: Al Zimin, Sr., Wayne, N.J.

[73] Assignee: Morton International, Inc., Chicago, Ill.

[21] Appl. No.: 09/150,398

[22] Filed: Sep. 9, 1998

Related U.S. Application Data

[63] Continuation-in-part of application No. 09/040,629, Mar. 18, 1998, abandoned.

[51] Int. Cl.[7] ..................................................... C10L 1/22
[52] U.S. Cl. .................................. 44/413; 44/425; 44/426
[58] Field of Search .............................. 44/413, 425, 426

[56] References Cited

U.S. PATENT DOCUMENTS

| | | | |
|---|---|---|---|
| Re. 30,650 | 6/1981 | Deubel et al. | 8/560 |
| 3,734,857 | 5/1973 | Moiso et al. | |
| 3,781,169 | 12/1973 | Deubel et al. | 8/560 |
| 3,991,044 | 11/1976 | Conley | 534/575 |
| 3,993,439 | 11/1976 | Deubel et al. | 8/560 |
| 4,209,302 | 6/1980 | Orelup | 44/425 |
| 4,776,886 | 10/1988 | Lorenz et al. | 106/31.28 |
| 5,055,567 | 10/1991 | Liechti et al. | 534/753 |
| 5,116,958 | 5/1992 | Liechti et al. | 534/591 |
| 5,306,343 | 4/1994 | Richardson, III et al. | 106/668 |
| 5,627,077 | 5/1997 | Dyllick-Brenzinger et al. | 44/328 |
| 5,738,693 | 4/1998 | Dyllick-Brenzinger et al. | 44/429 |

FOREIGN PATENT DOCUMENTS 0 751 208 A2   1/1997   European Pat. Off.

OTHER PUBLICATIONS

Ed; Merck & Co. Inc., N.J. 1983, p. 8, Windholz et al, *The Merck Index* "#47 Acetic Acid Glacial", 10th.
Chloride, "Chloride" & "Glacial", 4th, Ed., McGraw–Hill Book Co., N.Y., 1969, p.6,37–38,152,298, Grant, *Hackh's Chemical Dictionary*, "Acetic Acid", Ammonium.

*Primary Examiner*—Margaret Medley
*Attorney, Agent, or Firm*—Wayne E. Nacker; Charles N. Lovell; Gerald K. White

[57] ABSTRACT

A stabilized aqueous solution of a diazo compound has the formula:

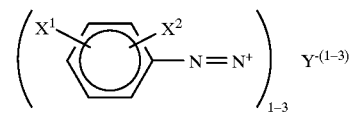

where $X^1$ is selected from nitro and chloro, $X^2$ is selected from nitro, chloro and hydrogen, and Y is an acid-derived anion. The solution has a pH of about 1.5 or below and a diazo concentration of about 2 wt % or less. The solution is useful as an extractant/developer for petroleum fuel markers.

6 Claims, No Drawings

STABILIZED AQUEOUS DIAZO SOLUTIONS

This is a continuation-in-part of application Ser. No. 09/040,629, filed on Mar. 18, 1998 now abandoned.

The present invention is directed to stabilized aqueous diazo solutions. Such solutions are useful as extractant/developers for petroleum fuel markers such as those described in U.S. Pat. No. 4,209,302, the teachings of which are incorporated herein by reference.

SUMMARY OF THE INVENTION

Above-referenced U.S. Pat. No. 4,209,302 describes markers for petroleum fuels of certain formulae. Such markers have the formulae:

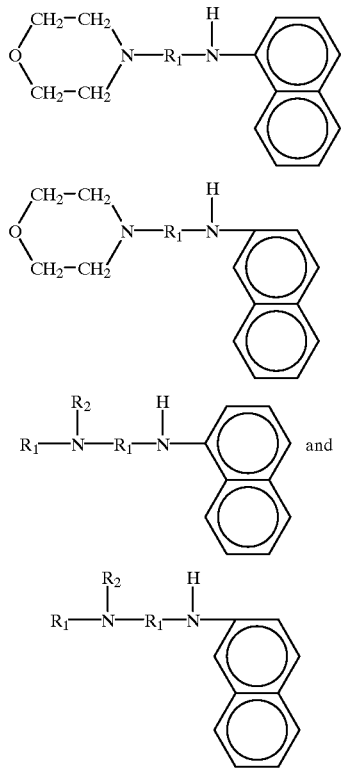

where $R_1$ and $R_2$ are hydrogen or alkyl having from one to twenty carbon atoms and $R_3$ is an alkylene group of from one to eight carbon atoms.

The markers described in U.S. Pat. No. 4,209,302 are identified by extracting the marker from the petroleum fuel with acidic aqueous extractant solution and then adding a stabilized S diazo of a compound such as the 2-chlor-4-nitroaniline. U.S. Pat. No. 4,209,302 clearly teaches that aqueous solutions of such diazo compounds are unstable. Accordingly, it has been necessary to provide an aqueous acidic extractant separate from a stabilized diazo solution, e.g., the diazo compound in glacial acetic acid. The extraction and color development might be done stepwise, or the two solutions might be mixed just prior to testing the petroleum fuel, but in any case, two solutions have been heretofore provided for field testing of tagged petroleum fuel.

Providing separate extractant and color development is undesirable from the standpoint of the complexity it adds to field testing. Also, as stabilized diazo compounds have some toxicity, it is desirable that they be provided in as dilute form as possible.

Thus, it is a primary object of the present invention to provide a stabilized solution of diazo compounds which act as both an extractant and a color developer.

SUMMARY OF THE INVENTION

In accordance with the present invention there is provided a stabilized aqueous solution of a diazo compound having the formula:

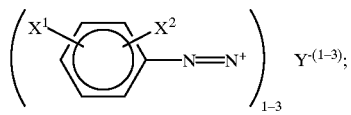

where $X^1$ is selected from nitro and chloro and $X^2$ is selected from nitro, chloro and hydrogen, and Y is an acid-derived anion, said solution having a pH of from about 0.5 to about 1.5 or below, preferably between about 1 and about 1.4, said solution having a diazo concentration of between about 0.01 and about 2 wt %, preferably about 1 wt % or less, more preferably about 0.25 wt % or less, most preferably about 0.1 wt % or less.

DETAILED DESCRIPTION OF CERTAIN PREFERRED EMBODIMENTS

Herein, and contrary to the teachings of U.S. Pat. No. 4,209,302, aqueous solutions of diazo compounds of the above formula have long-term stability, provided that the aqueous solution is very highly acidic (very low pH), and provided the diazo compound is sufficiently dilute. Such stabilized aqueous diazo solutions provide one-solution extraction/color development for petroleum fuel markers, such as those taught in U.S. Pat. No. 4,209,302. Because the diazo compounds in such solutions are at very dilute concentrations, they are considered acceptable by many government agencies without specialized precautions taken with respect to their shipping, handling, use and disposal. In fact, useful solutions in accordance with the invention may contain the diazo compound at such low concentrations that the diazo compound not even be listed on safety data sheets.

Particularly suitable compounds of the above-identified formula include, but are not limited to, diazotized 2-chlor-4-nitroaniline, 4-chlor-aniline, and 2-nitro-aniline.

Suitable acids for providing the anion(s) include, but are not limited to propionic acid, phosphoric acid, acetic acid, hydrochloric acid, nitric acid, sulfuric acid, formic acid, methane sulfonic acid ammonium chloride, glacial acetic acid, and mixtures thereof. Organic acids, such as propionic acid and acetic acid will not alone provide a pH of 1.5 or below, regardless of concentration. Accordingly, while these acids may be present, they must be present in conjunction with at least one other acid. For this reason, also, the stabilized glacial acetic acid formulations described in above-referenced U.S. Pat. No. 4,209,302, even if diluted will not provide a pH of 1 or below. Typically, the acid or mixture of acids will be present at between about 10 and about 40 wt % of the composition, most typically between about 20 and about 35 wt %.

Besides the small amount of diazo compound and the acid necessary to provide the low pH, substantially all of the rest of the composition is water. Generally water will be present at at least 40 wt %, more typically at least 50 wt % and above. Depending upon the amount of acid necessary to provide the desired low pH, the water content may be up to about 90 wt % of the solution.

A further advantage of the reagents in accordance with the invention over previous stabilized diazo reagents is that the reagents of the present invention do not freeze when cooled down to 0° C.

The invention will now be described in greater detail by way of specific examples.

EXAMPLE 1

A 0.099 wt % solution of diazotized 2-chloro-4-nitroaniline was prepared in a solution of 15 wt % ammonium chloride 15 wt % propionic acid 2.5 wt % phosphoric acid, balance water. (pH 1.10)

The diazo compound proved stable over a period of 34 weeks at room temperature.

EXAMPLE 2

A 0.25 wt % solution of diazotized 2-chloro-4-nitroaniline was prepared in a solution of 15 wt % ammonium chloride 15 wt % glacial acetic acid, balance water. (pH 1.25)

The diazo compound proved stable over a period of 34 weeks at room temperature.

EXAMPLE 3, COMPARATIVE

A concentrated solution of diazotized 2-chloro-4-nitroaniline was prepared containing 5 wt % of the dye, 10 wt % sulfuric acid and 85 wt % acetic acid. This was diluted with water to achieve a 0.099 wt % dye solution in water that provided a pH of 1.8 5.

The diazo compound destabilized after a period of 4 days.

This example shows that a primarily acetic acid formulation, even with a small amount of (stronger) sulfuric acid, when diluted, does not provide a sufficiently low pH to stabilize a dilute solution of the dye.

EXAMPLE 4, COMPARATIVE

A 0.25 wt % solution of diazotized 2-chloro-4-nitroaniline was prepared in water (pH=1.80).

The diazo compound destabilized after a period of 4 days.

What is claimed:

1. A stabilized aqueous solution consisting of between 0.01 and 2 wt % of a diazotized compound selected from the group consisting of 2-chloro-4-nitroaniline, 4-chloro-aniline and 2-nitro-aniline prepared by the process comprising:

adding said diazotized compound to a solution consisting of an acid mixture of propanic acid and acetic acid in an amount between about 20 and about 35%, 15 wt % ammonium chloride, balance at least about 50 wt % water, in an amount sufficient to produce a concentration between 0.01 and 2 wt % diazotized compound based on total solution, providing a pH of from about 0.05 to about 1.5 said aqueous solution having stability over a period of 34 weeks at room temperature.

2. A stabilized aqueous solution consisting of 0.099 wt % of diazotized 2-chloro-4-nitroaniline prepared by the process comprising:

adding diazotized 2-chloro-4-nitroaniline to a solution consisting of 15 wt % ammonium chloride, 15 wt % propionic acid, 2.5 wt % phosphoric acid, balance water, in an amount sufficient to produce a concentration of 0.099 wt % active diazotized 2-chloro-4-nitroaniline based on total solution, providing a pH of 1.0, said aqueous solution having stability over a period of 34 weeks at room temperature.

3. The solution according to claim 1 having a diazo compound concentration of about 1 wt % or less.

4. The solution according to claim 1 having a diazo compound concentration of about 0.25 wt % or less.

5. The solution according to claim 1 having a diazo compound concentration of about 0.1 wt % or less.

6. A stabilized aqueous solution consisting 0.25 wt % of diazotized 2-chloro-4-nitroaniline prepared by the process comprising:

adding diazotized 2-chloro-4-nitroaniline to a solution consisting of 15 wt % ammonium chloride, 15 wt % glacial acetic acid, balance water in an amount sufficient to produce a concentration of 0.25 wt % active diazotized 2-chloro-4-nitroaniline based on total solution, providing a pH of 1.25 said aqueous solution having stability over a period of 34 weeks at room temperature.

* * * * *